United States Patent
Shah

(10) Patent No.: US 6,902,725 B2
(45) Date of Patent: Jun. 7, 2005

(54) COLORED ANHYDROUS GEL ELEMENT

(75) Inventor: Syed Ashfaq Ali Shah, Ware (GB)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 10/272,853

(22) Filed: Oct. 17, 2002

(65) Prior Publication Data
US 2003/0091529 A1 May 15, 2003

Related U.S. Application Data

(63) Continuation of application No. PCT/GB01/01775, filed on Apr. 19, 2001.

(30) Foreign Application Priority Data

Apr. 19, 2000 (GB) .............................................. 0009577

(51) Int. Cl.⁷ .................................................. A61L 9/04
(52) U.S. Cl. ..................... 424/76.4; 424/76.1; 424/76.2; 424/76.3
(58) Field of Search ................................ 424/76.4, 400, 424/76.1, 76.2, 76.3; 523/102

(56) References Cited

U.S. PATENT DOCUMENTS

| 3,632,288 | A | * | 1/1972 | Niechwiadowicz et al. ......... 8/4 |
| 3,954,963 | A | | 5/1976 | Kuderna, Jr. |
| 3,954,964 | A | | 5/1976 | Kuderna, Jr. |
| 4,271,249 | A | * | 6/1981 | Gilliams et al. ............. 430/101 |
| 4,362,841 | A | | 12/1982 | Minatono et al. |
| 4,476,171 | A | | 10/1984 | Takeuchi |
| 5,060,858 | A | | 10/1991 | Santini |
| 5,419,879 | A | | 5/1995 | Vlahakis et al. |
| 5,439,100 | A | | 8/1995 | Gordon et al. |
| 5,556,835 | A | | 9/1996 | Inaoka et al. |
| 5,780,527 | A | * | 7/1998 | O'Leary ..................... 523/102 |
| 6,214,063 | B1 | * | 4/2001 | DeStefano et al. ........... 44/275 |

FOREIGN PATENT DOCUMENTS

| CA | 2250227 | 10/1997 |
| DE | 42 30 589 C1 | 2/1994 |
| DE | 43 01 912 A1 | 8/1994 |
| DE | 196 11 993 C1 | 4/1997 |
| EP | 1 121 159 B1 | 6/2003 |
| GB | 1010191 | 11/1965 |
| GB | 1428 109 | 3/1976 |
| GB | 2 039 740 A | 8/1980 |
| WO | WO 96/05870 A1 | 2/1996 |

* cited by examiner

Primary Examiner—Thurman K. Page
Assistant Examiner—Micah-Paul Young
(74) Attorney, Agent, or Firm—Akin Gump Strauss Hauer & Feld LLP

(57) ABSTRACT

A colored anhydrous gel element for perfuming or deodorizing air or enclosed spaces is provided. The element is formed by cross-linking a functionalized liquid polymer selected from maleinized polybutadiene, maleinized polyisoprene or a copolymer of ethylene and maleic anhydride with a cross-linking agent which contains at least one complementary functional group in the presence of a non-aqueous perfume or deodorizing base and a least one metal-free solvent dye which is soluble in the non-aqueous perfume or deodorizing base, or which is provided as a solution in a non-aqueous solvent which is compatible with the non-aqueous perfume or deodorizing base. The gel elements may be incorporated into devices which are used as air fresheners or deodorizers.

9 Claims, No Drawings

COLORED ANHYDROUS GEL ELEMENT

CROSS-REFERENCE TO RELATED APPLICATIONS

This application is a continuation of International Application No. PCT/GB01/01775, filed Apr. 19, 2001, which was published in the English language on Oct. 25, 2001 as International Publication No. WO 01/78794 A3 and the disclosure of which is incorporated herein by reference.

BACKGROUND OF THE INVENTION

The present invention relates to air care products and, in particular, to products which are capable of diffusing perfume or deodorizing components into the surrounding air.

The use of various devices for the diffusion of volatile compounds, for example perfumes, deodorizing compositions, insect repellents, and the like, into the atmosphere has become increasingly popular in recent years. For example, air-freshening devices or deodorizers are currently used in practically all households to mask bad odors, or to impart fragrances to the ambient air. Various different types of devices are known for the diffusion of volatile compounds into the surroundings. For example, devices of the spray type, such as aerosol sprays, may be used to dispense a liquid composition into the ambient air. Other devices comprise housings enclosing the active ingredients in liquid form. Typically, the diffusion of the active ingredients takes place through membranes permeable to the vapors of said ingredient, or through a wick which is placed in a reservoir containing the ingredients.

Solid state devices are also known which comprise solid materials or carriers impregnated with an active ingredient. Such devices may be formed of various materials which are capable of absorbing the ingredient and subsequently releasing it in a more or less controlled manner. Examples of such known materials include gels, such as agar-agar or sodium stearate gels, synthetic polymer resins, or blocks of mineral material, e.g., plaster or silica.

Solid state devices have the advantage that they are easy to handle and can be easily shaped. Typically, the solid state devices are enclosed within a housing with one or more grills which communicate with the surrounding air.

The main disadvantage with solid state devices is that the release of active ingredients from the blocks is not constant with time and drops dramatically over the lifetime of the device. Furthermore, such devices are inefficient, in that the device may cease to diffuse the active ingredient into the surrounding atmosphere when the outside of the block is spent, even though considerable amounts of the active ingredient may still reside within the core of the block. The residual active ingredient, such as perfume, is thus totally lost.

International patent application Publication WO 96/05870 discloses a device for perfuming, deodorizing or sanitizing air or enclosed spaces which comprises an anhydrous gel element. Such a device is capable of diffusing volatile substances at a relatively constant rate throughout the entire lifetime of the device and, furthermore, is capable of releasing substantially all of the volatile substance into the air or enclosed space within its effective lifetime.

The devices of WO 96/05870, although practically very useful, are unattractive since they are in the form of substantially colorless gels. However, because of the manner in which the gels are formed, it is difficult to incorporate dyes or colorants into the gels. Many dyes will not disperse within the system and result in unattractive, non-homogenous products, in which the dye is not uniformly dispersed therethrough. Neither the colorless gels of WO 96/05870 nor the non-homogenous colored gels would be attractive to the purchaser of such devices, which generally will be on display in the room or space which they are intended to perfume or deodorize.

BRIEF SUMMARY OF THE INVENTION

A colored anhydrous gel element for perfuming or deodorizing air or enclosed spaces is provided. The gel element comprises a cross-linked functionalized liquid polymer selected from the group consisting of maleinized polybutadiene, maleinized polyisoprene, and a copolymer of ethylene and maleic anhydride, wherein the functionalized liquid polymer is cross-linked with a cross-linking agent comprising at least one complementary functional group in the presence of a non-aqueous perfume or deodorizing base and at least one metal-free solvent dye, wherein the metal-free solvent dye is soluble in the non-aqueous perfume or deodorizing base or is provided as a solution in a non-aqueous solvent which is compatible with the non-aqueous perfume or deodorizing base.

A process for preparing the colored gel element as described above is also provided, which comprises cross-linking the functionalized liquid polymer with the cross-linking agent in the presence of the non-aqueous perfume or deodorizing base and at least one metal-free solvent dye.

DETAILED DESCRIPTION OF THE INVENTION

It has been found that homogenous, colored anhydrous gels can be prepared from the components as disclosed in WO 96/05870 if a very careful selection is made of the dyes for incorporation therein.

By the term "functionalized liquid polymer" as used herein is meant a material which is liquid at room temperature and which has a viscosity of not more than about 5 Pas at 25° C., preferably about 0.25 to about 1.0 Pas.

The functionalized liquid polymer which is used in the present invention is preferably a maleinized polybutadiene having a number average molecular weight of about 5,000 to about 20,000 or a maleinized polyisoprene having a number average molecular weight of about 200,000 to about 500,000. Examples of these materials are given in European published patent application EP-A-0023084. These materials are commercially available from Revertex Limited as Lithene™. Among the different grades of Lithene™ which are available, particularly good results have been obtained using Lithene™ N4-9000 10MA, in which 9000 represents the molecular weight of the polybutadiene before maleinization and 10MA indicates the degree of maleinization (in this case, 10 parts of maleic anhydride per 100 parts of polybutadiene, i.e., about 9.1%). Lithene™ N4-B-10MA and Lithene™ N4-5000-10MA are also particularly useful.

Alternatively, the liquid polymer may comprise a copolymer of ethylene and maleic anhydride, for example.

Examples of cross-linking agents which may be used in forming the anhydrous gels are as follows:

- alkylpropyldiamines having an ethoxylated or propoxylated higher aliphatic chain such as the products commercially available from Croda Chemicals Limited as Dicrodamet™;
- ethoxylated or propoxylated primary fatty amines available as Crodamet™, for example Crodamet™ O2 (oleylamine having 2 ethylene oxide units per molecule);

polyoxyalkylenediamines such as those commercially available from Huntsman Corporation as Jeffamine™, in particular the D and ED series, for example Jeffamine™ D-400, Jeffamine™ EDR-148, and Jeffamine™ D-2000; and polyoxyalkylenetriamines such as those commercially available from Huntsman Corporation as Jeffamine™, in particular the T series, for example Jeffamine™ T-403.

It is also possible to use as the cross-linking agent polybutadiene having a hydroxylic functionality known as HFPB (commercially available from Revertex Limited), which gellifies when admixed with maleinized polybutadiene. Sometimes, the use of specific catalysts allows a better control of the gel formation. Examples of such catalysts are tertiary amines (e.g., DAMA 1010, commercially available from Albermarle SA). Mixtures of Hycar CTBN 1300×21, which is an amine-terminated liquid polybutadiene/acrylonitrile copolymer commercially available from B. F. Goodrich, and maleinized polybutadiene are particularly advantageous.

The functionalized liquid polymer and the cross-linking agent are mixed in a molar ratio of about 3:1 to about 5:1, preferably about 1:1, based on the molar ratio of the functional groups which are present.

The perfume base which is used in the device of the invention may comprise any of the current bases used in perfumery. These can be discrete chemicals, but more often are more or less complex mixtures of volatile liquid ingredients of natural or synthetic origin. The nature of these ingredients can be found in specialized books of perfumery, e.g., in S. Arctander, *Perfume and Flavor Chemicals*, Montclair N.J., USA (1969) or *Perfumery*, Wiley-Intersciences, New York, USA (1994).

The perfume base may be replaced by a deodorizing base, such as a base which comprises a deodorizing composition.

The characteristic feature of all the compositions of the present invention is that the liquid polymer, cross-linking agent, and dye which are used in the preparation of the gellified composition are all soluble in the perfume or deodorizing base. Optionally, one or more of the liquid polymer, cross-linking agent or dye may be dissolved in a solvent which is compatible with the perfume or deodorizing base, but generally this is not necessary since the components will dissolve in the active base.

The perfume or deodorizing base is non-aqueous and will generally constitute about 50 to about 95% by weight, preferably about 60 to about 90% by weight, more preferably about 70 to about 85% by weight of the gel element.

Optional additives which may be included in the gel composition include plasticizers, such as diethylphthalate.

Examples of suitable classes of dyes which may be used in the present invention are monoazo dyes, diazo dyes, anthraquinone dyes and methine dyes, provided that the dyes are metal-free solvent dyes. Specific examples of dyes which may be successfully used in the present invention are:

| Chemical Characterization | Trademark (Manufacturer) |
| --- | --- |
| C.I. Solvent Red 27 | Fat Red 5B-02 (Clariant) |
| C.I. Solvent Red 111 | Sandoplast Red PFS (Clariant) |
| C.I. Solvent Yellow 14 | Fat Orange R-01 (Clariant) |
| C.I. Solvent Yellow 93 | Sandoplast Yellow 3G (Clariant) |
| C.I. Solvent Violet 13 | Iragon Violet SV113 (Ciba) |
| C.I. Solvent Violet 37 | Sandoplast Violet FBLP (Clariant) |

-continued

| Chemical Characterization | Trademark (Manufacturer) |
| --- | --- |
| C.I. Solvent Green 3 | Iragon Green SGR3 (Ciba) |
| C.I. Solvent Green 28 | Sandoplast Green G (Clariant) |
| C.I. Solvent Blue 104 | Sandoplast Blue 2B (Clariant) |

Dyes such as those listed above are generally available in powder form. Accordingly, in order to be useful in the present invention, the dye is generally soluble in the perfume or deodorizing base. However, it may be possible to use some dyes which are either not soluble in or insufficiently soluble in the base by using the dye as a concentrated solution in a non-aqueous solvent which is compatible with the base.

Generally, a relatively small amount of dye will be sufficient to color the anhydrous gel. For example, amounts of about 0.01 to about 1.0% by weight, typically about 0.05% by weight based on the gel element, may be used.

Many dyes cannot be used in the present invention. Examples of such dyes which are either not metal-free solvent dyes and/or are not soluble in the perfume or deodorizing base, are given below:

| Chemical Characterization | Trademark (Manufacturer) |
| --- | --- |
| C.I. Solvent Orange 63 | Hostalsol Red GG (Clariant) |
| C.I. Solvent Red 179 | Sandoplast Red 2GP (Clariant) |
| C.I. Solvent Red 89 | Savinyl Fire Red GLSP (Clariant) |
| C.I. Solvent Red 91 | Savinyl Red 3BLS P (Clariant) |
| C.I. Solvent Red 127 | Savinyl Pink 6BLS P (Clariant) |

The anhydrous gel element of the present invention may be used as the active element of a solid state air freshening or deodorizing device, with the gel element being incorporated within a housing with one or more grills which communicate with the ambient air.

Alternatively, the gel element may be formed in situ within the recesses or grooves of a solid casing or housing. This type of device does not require the use of a grill to cover the gel element. The recesses or grooves of the solid casing or housing are filled with the mixture of functionalized liquid polymer, cross-linking agent, perfume or deodorizing base, and dye, and the cross-linking reaction to form the gel takes place in situ. The gel so-formed thus adheres to the sides and/or bottom of the recesses or grooves in order to provide an integral structure.

The present invention will be further described with reference to the following specific, non-limiting Examples.

EXAMPLE 1

To a vessel containing 63.975 g of a perfume base (Lavandair 150.120D, commercially available from Firmenich SA, Geneva, Switzerland) was added 0.025 g of dye (Iragon Violet SVI13; commercially available from Ciba Speciality Chemicals, Switzerland) with stirring. 17.0 g of Lithene™ N4-B-10MA was then added manually and mixed. In another vessel 16.0 g of the perfume base (Lavender 150.120D) and 3.0 g of Jeffamine™ D-400 were mixed and then added to the original vessel with stirring. After about 5 minutes at room temperature, a purple gel resulted, encapsulating the perfume base. Gel setting was complete in about 20 minutes.

EXAMPLE 2

To a vessel containing 63.91 g of perfume base (Solar Splash 150.555; commercially available from Firmenich SA, Geneva, Switzerland) was added 0.09 g of dye (Sanoplast Yellow 3G; commercially available from Clariant UK Ltd, United Kingdom) with stirring. 17.0 g of Lithene™ N4-B-10MA was then added manually and mixed. In another vessel 16.0 g of the perfume base (Solar Splash 150.555), 1.12 g of Jeffamine™ EDR-148 and 1.88 g of diethyl phthalate were mixed and then added to the original vessel with stirring. After about 5 minutes at room temperature, a yellow gel resulted, encapsulating the perfume base. Gel setting was complete in about 20 minutes.

EXAMPLE 3

To a vessel containing 63.97 g of a perfume base (Summer Fruits 150.535; commercially available from Firmenich SA, Geneva, Switzerland) was added 0.03 g of dye (Fat Red 5B02; commercially available from Clariant UK Ltd, United Kingdom) with stirring. 17.0 g of Lithene™ N4-B-10MA was then added manually and mixed. In another vessel 16.0 g of the perfume base (Summer Fruits 15.535), 2.40 g of Jeffamine™ D-400, 0.22 g of Jeffamine™ EDR0148 and 0.38 g of diethyl phthalate were mixed and then added to the original vessel with stirring. After about 5 minutes at room temperature, a deep red gel resulted, encapsulating the perfume base. Gel setting was complete in about 20 minutes.

EXAMPLE 4

To a vessel containing 63.98 g of a perfume base (Nile Blossom 438.910; commercially available from Firmenich SA, Geneva. Switzerland) was added 0.02 g of dye (Iragon Green; commercially available from Ciba Speciality Chemicals, Switzerland) with stirring. 17.0 g of Lithene™ N4-B-10MA was then added manually and mixed. In another vessel 16.0 g of the perfume base (Nile Blossom 438.910), 2.40 g of Jeffamine™ D-400, 0.22 g of Jeffamine™ EDR-148 and 0.38 g of diethyl phthalate were mixed and then added to the original vessel with stirring. After about 5 minutes at room temperature, a blue/green gel resulted, encapsulating the perfume base. Gel setting was complete in about 20 minutes.

EXAMPLE 5 (COMPARATIVE)

To a vessel containing 63.97 g of a perfume base (Summer Fruits 150.535; commercially available from Firmenich SA, Geneva, Switzerland) was added 0.03 g of dye (Savinyl Fire Red GLSP; commercially available from Clariant UK Ltd, United Kingdom) with stirring. 170 g of Lithene™ N4-B-10MA was then added manually and mixed. In another vessel 16.0 g of the perfume base Summer Fruits 150.535), 240 g of Jeffamine™ D-400, 0.22 g of Jeffamine™ EDR-148 and 0.38 g of diethyl phthalate were mixed and then added to the original vessel with stirring. After about 5 minutes at room temperature, a gel resulted, but the color was not homogeneously distributed throughout, resulting in an unattractive aspect. Gel setting was complete in about 20 minutes.

EXAMPLE 6

To a vessel containing 3.998 g of a perfume base (Lavandair 150.120D; commercially available from Firmenich SA, Geneva, Switzerland) was added 0.00156 g of dye (Iragon Violet SVI13; commercially available from Ciba Speciality Chemicals, Switzerland) with stirring. 1.0625 g of Lithene N4-B-10MA was then added manually and mixed. In another vessel 1.0 g of the perfume base (Lavandair 150.120D) and 0.1875 g of Jeffamine™ D-400 were mixed and then added to the original vessel with stirring. Once a homogeneous mix was attained, the mixture was added to a suitable decorative device containing grooves which the liquid mix could run through. After about 5 minutes at room temperature, a purple gel, in the shape of the device, resulted, encapsulating the perfume base. Gel setting was complete in about 20 minutes.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A device which comprises an air freshener or deodorizer comprising a homogeneous colored anhydrous gel element, the element comprising a cross-linked functionalized liquid polymer selected from the group consisting of maleinized polybutadiene, maleinized polyisoprene, and a copolymer of ethylene and maleic anhydride, wherein the functionalized liquid polymer is cross-linked with a cross-linking agent comprising at least one complementary functional group in the presence of a non-aqueous perfume or deodorizing base and at least one metal-free solvent dye, wherein the metal-free solvent dye is soluble in the non-aqueous perfume or deodorizing base, or is provided as a solution in a non-aqueous solvent compatible with the non-aqueous perfume or deodorizing base and is selected from the group consisting of a monoazo dye, a diazo dye, an anthraquinone dye, and a methine dye.

2. The device according to claim 1, wherein the at least one metal-free solvent dye is selected from the group consisting of C.I. Solvent Red 27, C.I. Solvent Red 111, C.I. Solvent Yellow 14, C.I. Solvent Yellow 93, C.I. Solvent Violet 13, C.I. Solvent Violet 37, C.I. Solvent Green 3, C.I. Solvent Green 28, and C.I. Solvent Blue 104.

3. The device according to claim 1, wherein the at least one metal-free solvent dye comprises about 0.01 to about 1.0% by weight of the gel element.

4. The device according to claim 1, wherein the non-aqueous perfume or deodorizing base comprises about 60 to about 95% by weight of the gel element.

5. The device according to claim 4, wherein the non-aqueous perfume or deodorizing base comprises about 70 to about 80% by weight of the gel element.

6. The device according to claim 1, wherein the functionalized liquid polymer comprises a maleinized polybutadiene having a number average molecular weight of about 5,000 to about 20,000, or a maleinized polyisoprene having a number average molecular weight of about 200,000 to about 500,000.

7. The device according to claim 1, wherein the cross-linking agent is selected from the group consisting of an alkylpropylamine, an ethoxylated or propoxylated primary fatty amine, a polyoxyalkylenediamine, and a polyoxyalkylene triamine.

8. The device according to claim 1, wherein the functionalized liquid polymer and the cross-linking agent are soluble in the non-aqueous perfume or deodorizing base.

9. A process for preparing the device according to claim 1 comprising preparing the colored anhydrous gel element by cross-linking the functionalized liquid polymer with the cross-linking agent in the presence of the non-aqueous perfume or deodorizing base and the at least one metal-free solvent dye.

* * * * *